(12) United States Patent
Richards et al.

(10) Patent No.: US 8,691,295 B2
(45) Date of Patent: Apr. 8, 2014

(54) DIETARY SUPPLEMENT FOR VASCULAR HEALTH

(71) Applicants: John Michael Richards, Bowie, MD (US); John Francis Henry, Woodbridge, VA (US); Keith Eugene Mathews, Jr., Lanham, MD (US)

(72) Inventors: John Michael Richards, Bowie, MD (US); John Francis Henry, Woodbridge, VA (US); Keith Eugene Mathews, Jr., Lanham, MD (US)

( * ) Notice: Subject to any disclaimer, the term of this patent is extended or adjusted under 35 U.S.C. 154(b) by 0 days.

(21) Appl. No.: 13/662,399

(22) Filed: Oct. 26, 2012

(65) Prior Publication Data

US 2013/0189297 A1    Jul. 25, 2013

Related U.S. Application Data

(60) Provisional application No. 61/551,807, filed on Oct. 26, 2011.

(51) Int. Cl.
*A01N 65/00* (2009.01)

(52) U.S. Cl.
USPC .......................................................... 424/725

(58) Field of Classification Search
None
See application file for complete search history.

(56) References Cited

U.S. PATENT DOCUMENTS

2003/0206978 A1 * 11/2003 Sherwood et al. ............ 424/728

* cited by examiner

*Primary Examiner* — Michael Meller
(74) *Attorney, Agent, or Firm* — Michael D. Eisenberg

(57) ABSTRACT

The present invention relates to an herbal dietary supplement to promote vascular health. The dietary supplement comprises L-Arginine, L-Citrulline, Ginkgo Biloba, Horse chestnut, Red Yeast Rice and Cayanne Pepper.

1 Claim, 1 Drawing Sheet

| |
|---|
| L Arginine |
| L Citrulline |
| Ginkgo Biloba |
| Horse Chestnut |
| Red Yeast Rice (<0.4% active ingredient) |
| Cayenne (Capsicum) |

DIETARY SUPPLEMENT FOR VASCULAR HEALTH

CROSS-REFERENCES TO RELATED APPLICATIONS

This application claims priority from U.S. Provisional Application Ser. No. 61/551,807 filed Oct. 26, 2011, which is hereby incorporated herein by reference in its entirety.

TECHNICAL FIELD

The present invention relates to a dietary supplement composition for the promotion of vascular health.

BACKGROUND OF THE INVENTION

The present invention relates to an herbal dietary supplement to promote vascular health. Most pharmaceuticals originate from an increased concentration of natural plants and herbs. The process however creates many undesirable side effects. Concerns among the aging population of the present include memory loss, and heart attacks. The present invention ameliorates both ailments.

BRIEF SUMMARY OF EMBODIMENTS OF THE INVENTION (1) A dietary supplement comprises 1-Arginine, L-Citrulline, Horse chestnut, Red Yeast Rice and Cayanne Pepper.

(2) In a variant, the dietary supplement comprises equal parts l-Arginine, L-Citrulline, Horse chestnut and Red Yeast Rice.

(3) In another variant, the dietary supplement comprises: two parts of Cayanne Pepper for one part of each l-Arginine, L-Citrulline, Horse chestnut, Red Yeast Rice and Cayanne Pepper.

(4) In a further variant, the dietary supplement further comprises Ginkgo Biloba.

(5) In yet another variant, the dietary supplement comprises as a percentage of weight the following components: L-Arginine from 2.849003% to 70.25761% by weight; L-Citrulline from 1.121076% to 42.19409% by weight; Ginkgo Biloba from 0.614754% to 7.843137% by weight; Horse chestnut from 0.107181% to 25.5102% by weight; Red Yeast Rice from 6.507592% to 57.97101% by weight; and Cayanne Pepper from 7.911392% to 80.4829% by weight.

BRIEF DESCRIPTION OF THE DRAWINGS

FIG. 1 is a listing of compositions that comprise the dietary supplement of the present invention.

DETAILED DESCRIPTION OF THE EMBODIMENTS OF THE INVENTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

The present invention is directed toward an herbal dietary supplement to promote vascular health.

In a variant, a 3000 mg specimen of the supplement is comprised of the following:
 500 mg of L-Arginine
 500 mg of L-Citrulline
 500 mg of Horse chestnut
 500 mg of Red Yeast Rice
 1000 mg of Cayanne Pepper (Capsicum)

Preferably, the 3000 mg supplement is compounded into two tablets with enteric coating and minimal fillers and binders and bottled and labeled in quantities of 120.

In a preferred embodiment, the supplement is ingested by a patient twice daily, and the supplement is formed into two tablets, which together comprise:
 1000 mg of L-Arginine
 1000 mg of L-Citrulline
 240 of Ginkgo Biloba
 1000 mg of Horse chestnut
 1200 mg of Red Yeast Rice (<0.4% active ingredient)
 2000 mg of Cayanne Pepper (Capsicum)

In a preferred variant, the supplement comprises by percentage weight:
 15% of L-Arginine
 15% mg of L-Citrulline
 3% of Ginkgo Biloba
 15% mg of Horse chestnut
 18% mg of Red Yeast Rice (<0.4% active ingredient)
 30% mg of Cayanne Pepper (Capsicum)

A 30 day supply consists of a person taking two tablets upon waking in the morning and two additional tablets at bedtime in the evening for a total of 4 tablets per day.

Assuming a single table of the supplement is formed, for ingestion twice daily, the composition may vary, with a lowest mg and highest mg for each component as follows:
 400 mg-6 gm of L-Arginine
 1200 mg-2000 mg of L-Citrulline
 120 mg-240 mg of Ginkgo Biloba
 20 mg-1000 mg of Horse chestnut
 1200 mg-2400 mg of Red Yeast Rice (<0.4% active ingredient)
 1000 mg-8000 mg of Cayanne Pepper (Capsicum)

This information is summarized below in Table 1, and includes a maximum allowable daily dose.

TABLE 1

| Ingredient | Dosage | Dosage Range | % and Range | Max |
|---|---|---|---|---|
| L Arginine | 1000 mg BID | 400 mg-6 gm qD | 15% of QS | 6 gm qD |
| L Citrulline | 1000 mg BID | 200 mg-2000 mg qD | 15% of QS | 3 gm qD |

TABLE 1-continued

| Ingredient | Dosage | Dosage Range | % and Range | Max |
|---|---|---|---|---|
| Ginkgo Biloba | 240 mg BID | 120 mg-240 mg qD | 3% of QS | 1 gm qD |
| Horse Chestnut | 1000 mg BID | 20 mg-1000 mg qD | 15% of QS | 1 gm qD |
| Red Yeast Rice (<.4% active ingredient) | 1200 mg BID | 1200 mg-2400 mg qD | 18% of QS | 5 gm qD |
| Cayenne Capsicum | 2000 mg BID | 1000 mg-8000 mg qD | 30% of QS | 8 gm qD |

Table 2 is derived from the information in Table 1, and provides the minimum and maximum percentage of the various ingredients of a specimen of the supplement.

TABLE 2

|  | Lowest Percentage By Weight | Highest Percentage By Weight |
|---|---|---|
| L-Arginine | 2.849003 | 70.25761 |
| L-Citrulline, | 1.121076 | 42.19409 |
| Ginkgo Biloba | 0.614754 | 7.843137 |
| Horse chestnut | 0.107181 | 25.5102 |
| Red Yeast Rice | 6.507592 | 57.97101 |
| Cayanne Pepper | 7.911392 | 80.4829 |

Clinical evidence clearly indicates the positive therapeutic effects of Horse Chestnut (aecin) on peripheral vascular disease, leg edema, varicose veins, and chronic venous insufficiency. It is considered equal to or better than embolic stocking applied to lower extremities at reducing peripheral edema. Additional anti-inflammatory effects promote improved peripheral blood flow.

L Arginine and L Citrulline via the nitric oxide enzymatic cascade has a positive effect on endothelial repair and smooth muscle relaxation therefore a decrease in BP via blood vessel dilatation.

Ginkgo via clinical evidence has shown activity for increased cerebral vascular blood flow and anticoagulation. Gingko activity has shown to have a wide range of positive somatic responses, however for this discussion; the effects are limited to those associated with CVS.

Red Yeast Rice (red rice koji), with the active components of monacolin K associated with lovostatin has significant cholesterol lowering capabilities. Clinical studies have indicated that prescription dosages have a 21%-36% lowering of HDL cholesterol over controls. Additional back cross studies show that micro-dosing carries similar cholesterol lowering properties without the significant adverse effects of myalgia and muscle weakness associated with long term statin use.

Cayenne (Capsicum) has been documented to aid in several medical maladies. For example, it has been shown to aid with indigestive, arthritis, colic, menstrual cramps and symptoms associated with URTI. With its incorporation in the supplement, cayenne's effect on the cardiovascular system and large blood vessels though vasodilatation has been shown to have effects on ischemic heart disease and hypertension. Some studies and anecdotal evidence have indicated its usefulness in treatments immediately after significant cardiac events.

The supplement was developed to assist in the management of major cardiovascular maladies. A major problem addressed by the supplement is the management and control of hypertension. The supplement's ingredients are documented to have positive effects on lowering systemic blood pressure by having a vasodilatation effect on the peripheral vasculature much like hydralazine; causing relaxation of smooth muscles. Unlike Hydralazine which accomplishes this through interference of the calcium inside the smooth muscles, because contraction cannot occur without calcium movement thus relaxation, the supplement achieves this through its active ingredients L-arginine and L-citulline which are direct precursors in the synthesis of nitric oxide which plays a central role in endothelial angiogenesis via a cascade enzymatic sequence resulting in a potent vasodilatation effect. Aside from this, arginine and citulline also act via the nitric oxide reaction as a significant mechanism for endothelial cell repair, a benefit not commonly found in any prescribed medication.

The supplement has an ingredient, horse chestnut, effective in the treatment of peripheral edema and venous insufficiency. Aescin, the active component in horse chestnut appears to have effects on endothelial nitric oxide and calcium oxide permeability. It may also induce the prostaglandin F2a. These appear to have significant anti-inflammatory and vasodilitation. This mechanism can to associated with repair of endothelial cells. Pentoxifylline (trental) appears to have significant therapeutic utility for intermittent claudication resulting from obstructed veins and arteries. Pentoxifylline is a methylated xanthine derivative, competitive nonselective phosphodiesterase inhibitor. Certain components here would also have positive effects on nitric oxide utility as well.

The supplement also has a significant adjunctive therapy for hypercholesterolemia. Red yeast rice or red rice koji owing to the content of monacolin K (lovastatin). Clinically statins are important because of the inhibitory effects on cholesterol synthesis through enzymatic blocking of HMG-CoA reductase. There are studies which indicate that the micro-dosing content of statins in monacolin K have better clinical outcomes than reported outcomes for prescription drugs.

Considering the combination L arginine, citrulline, horse chestnut, and red yeast rice (red rice koji) combines therapeutic effects of hydralazine, trental, mevacor and furosemide. Additionally the enhanced effects of Gingko biloba and cayenne (capsicum) has an additive effect of cerebral vascular profusion, vasodilatation and anticoagulation further augments the positive therapeutic effects.

While various embodiments of the present invention have been described above, it should be understood that they have been presented by way of example only, and not of limitation Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A dietary supplement, consisting essentially of:
L-arginine, L-citrulline, horse chestnut extract, red yeast rice extract, cayenne pepper extract and ginkgo biloba extract.

* * * * *